United States Patent [19]

Holmquist et al.

[11] 4,399,217
[45] Aug. 16, 1983

[54] PROCESS AND A DEVICE FOR THE DETERMINATION OF SERUM LIPOPROTEINS

[75] Inventors: Leif T. Holmquist; Lars A. Carlson, both of Stockholm, Sweden

[73] Assignee: Laboratoires Goella, Paris, France

[21] Appl. No.: 224,538

[22] PCT Filed: Apr. 30, 1980

[86] PCT No.: PCT/FR80/00067

§ 371 Date: Dec. 10, 1980

§ 102(e) Date: Dec. 10, 1980

[87] PCT Pub. No.: WO80/02460

PCT Pub. Date: Nov. 13, 1980

[30] Foreign Application Priority Data

May 2, 1979 [FR] France ............................ 79 11082

[51] Int. Cl.³ .................... G01N 33/92; G01N 33/54
[52] U.S. Cl. .......................................... 435/7; 424/85;
424/88; 435/4; 435/21; 435/25; 435/28;
435/188; 436/71; 436/518; 436/524; 436/808;
422/61
[58] Field of Search ................... 23/230 B, 230 R;
424/12, 88, 85, 177; 435/7, 4, 21, 25, 28, 188;
436/518, 524, 71

[56] References Cited

U.S. PATENT DOCUMENTS

| 4,002,532 | 1/1977 | Weltman et al. | 424/12 |
| 4,190,496 | 2/1980 | Rubenstein et al. | 435/7 |
| 4,230,805 | 10/1980 | Singh et al. | 435/188 |
| 4,241,177 | 12/1980 | Singh et al. | 435/7 |

FOREIGN PATENT DOCUMENTS

| 2811228 | 9/1978 | Fed. Rep. of Germany | 435/7 |
| 2385099 | 11/1978 | France | 435/7 |
| 1595017 | 8/1981 | United Kingdom | 103/52 |

OTHER PUBLICATIONS

Immunochemistry, vol. 8, pp. 871-874, (1971), Engvall et al.
Chemiker-Zeitung, vol. 103, pp. 53-68, (1979), Strecker et al.
Clinical Chemistry, vol. 24, No. 3, (1978), pp. 455-459, Fruchart et al.
Chem. Abstracts, 85(13), p. 253, Abstract 89646r, G. R. Thompson et al., Published Sep. 27, 1976.
Chem. Abstracts, 88(23), p. 267, Abstract 166261c, J. C. Fruchart et al., Published Jun. 5, 1978.
Chem. Abstracts, 89(5), p. 264, Abstract 39042c, J. C. Fruchart et al., Published Jul. 31, 1978.
Clinical Chemistry, vol. 22, No. 8, pp. 1243-1255, G. B. Wisdom et al., 1976.

Primary Examiner—Benjamin R. Padgett
Assistant Examiner—M. Morkowitz

[57] ABSTRACT

The invention relates to a process for the determination of serum lipoproteins by an immuno-enzymatic method. The process of the invention consists in reacting a specific antibody of the apoprotein whose amount is to be measured, fixed on a support, with, on the one hand, the compound for coupling the corresponding lipoprotein with an enzyme and, on the other hand, the analyzed sample. The amount of enzyme fixed is then an inverse function of the apoprotein content of the sample. The support with the products which are fixed thereto are separated from the rest of the reagents and the activity of the enzyme of the support is measured which is compared with standard measurements.

The process is useful for serum analyses, particularly for early detection of cardiovascular disease risks.

17 Claims, 1 Drawing Figure

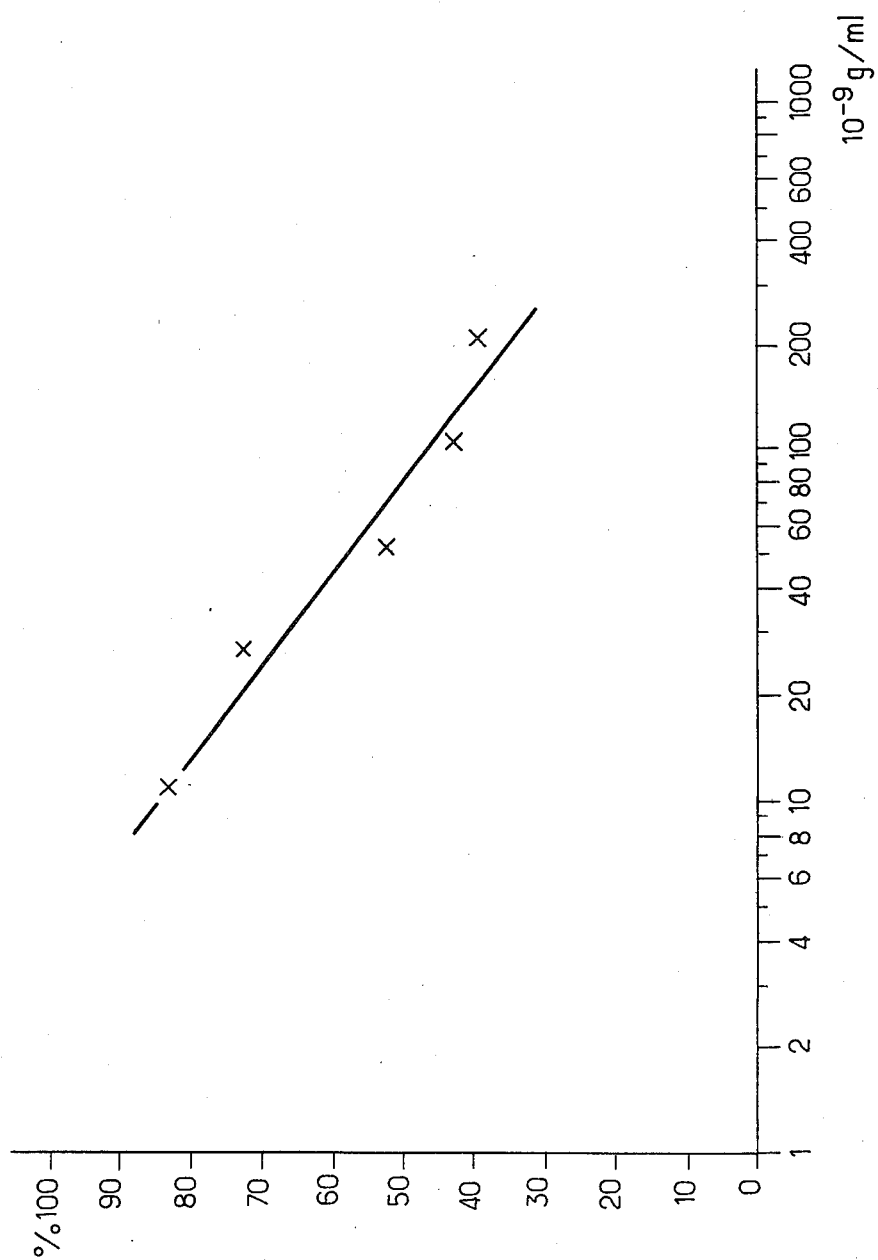

PROCESS AND A DEVICE FOR THE DETERMINATION OF SERUM LIPOPROTEINS

The invention relates to a process for the determination of serum lipoproteins as well as devices for implementing this process. More precisely, the process of the invention is intended for the determination of the protein components of serum lipoproteins.

Recent epidemiological studies on the risks of appearance of cardiovascular illnesses have shown the advantage of determining not only the global amount of serum lipoproteins but also and especially by making a distinction according to the group to which these lipoproteins belong and, within these groups, according to the type of apoprotein ($C_1$, $C_2$, $C_3$, E, B, $A_1$, $A_2$). Traditionally, the three principal groups considered are the VLDL, LDL and HDL, these abbreviations corresponding to the English terms "very light density lipoprotein", "light density lipoprotein" and "high density lipoprotein". This designation refers to the way in which the separation is accomplished in ultracentrifugation separation techniques.

The importance of this distinction resides in the fact that close correlations have been able to be established, on the one hand, between the proportions of these types of lipoproteins and, on the other hand, the risk of appearance of the illnesses in question. Very succinctly, the risk is all the greater the higher the proportions of VLDL and LDL (and of apoprotein B) and, on the contrary, all the lower the higher the proportion of HDL.

For measuring the proportions of the different types of lipoproteins, several techniques have been previously proposed, which comprise separation of the different fractions of lipoproteins from the sample analyzed then the determination of the fractions thus separated. The principal difficulty with this kind of analysis resides in the separation of the different fractions. Thus, ultracentrifugation separation methods are not practicable for analyses carried out in a large number. For these routine analyses the only methods used at present comprise separation by selective precipitation. The accuracy of these methods rests particularly on the specificity of the precipitation carried out in earlier researches, and every effort has been made to perfect means improving this specificity. Appreciable improvements have been able to be obtained in this field by an appropriate choice of conditions and agents used for this precipitation. Furthermore, the traditional methods do not allow separation of each type of apoprotein within the same group. However, an additional increase of accuracy and sensitivity of measurement, while maintaining great facility of use and the possibility of determining the proportion of each apoprotein, was desirable.

The pesent invention proposed then providing means for effecting a determination of the different lipoproteins or fractions of lipoproteins, which is at one and the same time simple, very sensitive and accurate.

This aim was reached, in accordance with the invention, by using, for the determination of serum lipoproteins, a process combining immunological and enzymatic techniques and presenting the specificity of the one kind and the great sensitivity of the other.

According to the invention, the process consists in reacting, in conditions appropriate for the formation of a complex of the antibody-antigen type, on the one hand, a given amount of a specific antibody of the apoprotein(s) whose quantity it is desired to determine, this antibody being fixed on a solid support inert with respect to the reactive medium in which the antibody-antigen complex is formed and with respect to the medium in which the enzymatic activity is subsequently measured, on the other hand, the serum sample to be analyzed and a given amount of a compound for coupling the lipoprotein of the type of the one whose content is to be determined, or of several lipoproteins among which the one whose quantity is to be determined, with an enzyme which does not impair the formation of the antigen-antibody complex; with this latter accomplished, the reagents not fixed on the solid support phase are eliminated and the enzymatic activity of the complex attached to the support is measured.

The principal of the measurement is the following. The antigens present in the sample to be analysed and in the compound coupled to the enzymes are in competition in the formation of the antigen-antibody complex. The amount of enzyme in the complex formed depends on the amount of antigen in the sample analyzed, and is all the lower the greater this latter. After elimination of the reagents not fixed on the support, the measurement of the enzymatic activity of the support constitutes then indirectly a determination of the amount of the protein, present in the analyzed sample, corresponding to the specific antibody fixed on the support.

The separation of the antigen-antibody complex, and the measurement of activity which follows thereafter, is all the easier by operating a heterogeneous phase. For reasons of convenience, it is advantageous to use the antibodies in the heterogeneous phase, which is obtained by fixation thereof on the support. It is however also prossible to accomplish the heterogeneity of the phases after formation of the antigen-antibody complex (or simultaneously) according to the usual techniques used in enzymatic analysis: precipitation, selective adsorption, etc.

In all cases it is necessary, in accordance with the invention, to end up with a heterogeneous form fixing the complex and which is easily separable from the components of the mixture left in the liquid phase. In the rest of the description, only the case of the antibodies fixed on a solid support is developed. This case represents in fact, as has been said, the most convenient and the simplest implementation.

A practical way consists in using, for support of the antibodies, the very material of the vessel in which the complexation reaction is carried out. Thus, once this reaction is finished, it is sufficient to evacuate the reaction medium; the vessel containing the complex may then serve directly for the measurement of the selected enzymatic activity, by introduction of the appropriate substrate.

If the fixation of the antibody on the vessel constitutes a preferred form, it may also be fixed on a support independent thereof. In this sense, any support capable of fixing the antibodies, whatever its form, may be used. It is however preferable to choose the support so that it allows good contact with the reaction medium, on the one hand and, on the other hand, may be easily separated once the reaction is finished. Forms such as grains, balls, beads, are particularly suitable.

To implement the determination process of the invention, it is necessary to use a compound formed by the coupling of the apoprotein and an enzyme. The reaction only takes place, of course, between the antibodies and the corresponding antigens. Only the apoprotein-enzyme corresponding to the fixed antibody is capable of reacting. However, considering the difficulty and consequently the cost, of preparing and purifying isolated apoproteins, it is advantageous to use not the compound for coupling an enzyme with an apoprotein, but that resulting from coupling with a set of serum apoproteins. The apoproteins-enzyme mixture plays the same role with respect to the specific antibody as the isolated apoprotein.

It is convenient to use as apoprotein-enzyme coupling compound the one resulting from the fixation of the enzyme on the lipoprotein fractions such as obtained by traditional fractionation techniques.

Advantageously, the amounts of antibody and of apoprotein-enzyme compound are adjusted so that the determination presents a maximum sensitivity. Advantageously, these amounts are close to equivalence.

We will now consider in more detail each of the means used for implementing the process in accordance with the invention.

(1) The apoproteins

Lipoproteins are formed, as their name indicates, from a lipidic part and a protein part, the apoprotein. Some of these apoproteins are characteristic of the previously-indicated lipoprotein fractions. The apoproteins $C_1$, $C_2$, $C_3$ are borne essentially by the VLDL; apoprotein B is borne by the LDL and the VLDL; apoproteins $A_1$ and $A_2$ are borne by the HDL; apoprotein E appears in some cases of hyperproteinemies (in the VLDL fraction). All these apoproteins are carriers of specific immunogenic determinants. The specificity of these determinants in the reaction forming the complex enables the amount of a given apoprotein within a complete serum sample to be determined, i.e. within a sample on which it is not necessary to carry out previously separation operations.

The preparation of purified apoproteins required for obtaining the corresponding antibodies is made from serum lipoprotein fractions traditionally separated by ultracentrifugation on a density gradient.

Once separated the lipoprotein fractions are subjected to delipidation and the separate apoproteins are isolated by an equally traditional method such as chromatography, electrophoresis, etc.

Furthermore, the fractionated serum lipoproteins also serve in the preparation of lipoprotein-enzyme coupling compounds.

(2) The specific antibodies

They are obtained in accordance with a traditional method, by immunization of an animal with respect to the isolated human apoprotein. Different methods may be used for the vaccination leading more or less rapidly to a more or less high specific antibody content.

For preparing this antiserum containing these antibodies, rabbits are advantageously used, but other animals may also be used: goat, sheep, horse, guinea pig, etc.

The specific antigens are administered in a sufficient does for generating an immunitary response. If necessary the antigen is administered with an additive stimulating the response. Repeat administrations may also be carried out for amplifying the formation of the antibodies. The blood of the immunized animal is then taken and the serum containing the antibodies is separated. To facilitate the subsequent operations, it may be advantageous to isolate the immunoglobulines of this serum by known methods, for example by precipitation.

(3) Fixation of the antibodies on the support.

The fixation must comply with several requirements.

The antibody must first of all be stably fiixed, i.e. it must not be freed on contact with the media used for the formation of the antigen-antibody complex.

The fixation must not appreciably impair the reactivity of the antibody with respect to the antigen.

Several means for fixing on a solid support may be envisaged. These means depend for a large part on the nature of the support material. In a simplified way, two sorts of fixation may be envisaged: a fixation using stable chemical bonds, particularly covalent bonds for the case where the material presents functional groups capable of fixing the antibodies, fixation by adsorption on the support material.

Very diverse materials may be used as support; however, because of their convenience in use and their low cost, polymer materials such as polystyrene, polyamide, polyethylene, etc. are advantageously used.

The adsorption capacity of these materials is often low. In other words, the amount of antibodies fixed, and consequently of enzyme, in the complex, is low considering the volume of the support. To increase the adsorption, it is possible, in accordance with the invention, to coat the material with a film of a material having a higher adsorption power, and the same inertia with respect to the reactive medium.

Whatever the mode of fixation chosen, it is necessary to introduce a constant amount of antibodies during the different analyses and standardizing operations. When the fixation is made on the wall of the analysis vessel, the amount of antibodies fixed is adjusted by the identity of the different vessels used and that of the antibody solutions with which they are placed in contact during fixation.

If a support in the form of beads or similar corpuscles is used, attention should be paid that an equal amount of homogeneous elements is introduced into the vessel at the time of the analysis.

(4) Lipoprotein-enzyme coupled compound.

The enzyme chosen must comply with several conditions to allow practical use.

It must first of all be stable. The reagents must be able to be kept for relatively long periods without undergoing appreciable degradation.

It must present a significant activity easy to quantify and especially this activity must not be exerted with respect to the components of the medium of immunochemical reaction resulting in the antigen-antibody complex. Nor must the enzyme be found in the serum constituents.

Among the usable enzymes complying with these conditions, alkaline-phosphatase, peroxydase or galactose oxydase may be advantageously used.

The coupling of the enzyme with the lipoproteins (or apoproteins) is carried out in accordance with conventional techniques for fixing enzymes on proteins.

The coupliing is conducted so that neither the activity of the enzyme nor especially the reactivity of the apoprotein (with respect to the antibodies) are profoundly modified.

Different coupling methods are possible. It is preferred to use coupling accomplished with a dialdehyde, particularly glutaraldehyde. Another advantageous form of coupling consists in forming a Schiff base.

According to another aspect, the invention also relates to the devices used for implementing the process, and particularly the products and necessary reagents gathered together in the form of a practical presentation.

This presentation comprises at least one specific antibody of a serum apoprotein and the corresponding lipoprotein-enzyme complex(es), the different reagents being in proportioned amounts and isolated from each other under conditions appropriate for their conservation.

Advantageously, in this presentation, the antibody or antibodies are fixed on vessels intended for the analysis. These vessels are preferably tubes or tanks directly usable, without transfer, in the measuring apparatus, i.e. in a spectrophotometer or in a colorimeter.

Plates of the type used for microtitrations and having a multiplicity of cupules, on which the antibodies are fixed, may also be used, in particular for determination in series.

The receptacles containing the antibodies, as also the lipoprotein-enzyme complexes, are preserved sheilded from the light and in sealed packings.

The lipoprotein-enzyme complex is preferably in solution. As we pointed out previously, depending on the type of apoprotein analyzed, it is preferable to use the product for coupling the enzyme with the serum lipoprotein fractions resulting from the ultracentrifugation separation. Thus, an enzyme-VLDL complex is advantageously used for the analysis of the apoprotein $C_1$, $C_2$, $C_3$ or E, an enzyme-LDL complex for quantity determination of apoprotein B, and an enzyme-HDL complex for apoprotein $A_1$ or $A_2$.

The enzyme-lipoprotein complexes are advantageously in proportions substantially equivalent to the amounts of the corresponding antibodies. They may be presented in the form of unit doses, in ampoules for example, or in a bottle containing the proportions required for the whole of the receptacles contained in the presentation.

The presentation in accordance with the invention contains furthermore primary or secondary standard reagents such as previously described and formed consequently either by a purified apoprotein or by a lipoprotein fraction.

These standards are advantageously presented in lyophilized form and may be reconstituted by addition of distilled water.

The presentation may also contain the reagents required for measurement of the enzymatic activity.

The presentation may finally contain bottles for the measuring medium and/or the washing medium used in accordance with the process.

The following examples illustrate in a detailed way different characteristics of the process and of the device according to the invention.

EXAMPLE 1

Preparation of the specific antibodies

The mode of operation is by immunization of rabbits with apoprotein of human origin obtained by preparative ultracentrifugation.

50 µg of antigens emulsified in the complete additive of Freund are injected intradermally at several points. A repeat is given under the same conditions two months later.

The blood is collected after 8 months by cardiac puncture and the serum is isolated. The immunoglobulines are separated from this latter by selective precipitation with ammonium sulphate.

EXAMPLE 2

Fixation of the antibodies on the walls of the vessel

In what follows, the vessels used are parallepipedic tanks made from "crystal" polystyrene.

Three modes of fixation have been carried into effect.
(a) By covalent bond.

A superficial nitration of the polystyrene is effected by contact with an $HNO_3$-$H_2SO_4$ mixture, followed by reduction of the nitro groups into amino groups. The amino groups are then diazotized and the diazo formed is coupled with free amine groups of the antibody to be fixed.

(b) By adsorption at the surface of the tank.

2 µg of proteins of the immunoglobuline fraction are added to 1 ml of sodium carbonate buffer pH=9.8. After incubation of 3 hours at 37° C., the liquid content is eliminated and vessels are washed three times with saline phosphate buffer at pH 7.4, at 4° C., containing 0.065% of a surface-active agent such as Tween 20 or Triton×100.

(c) By adsorption on a cellulose film.

To obtain higher adsorption it is possible to deposit on the surface of the receptacle an adsorbing film.

For this purpose 1.5 g of cellulose (or of a cellulose derivative such as cellulose nitrate or bromo-acetyl-cellulose) is dissolved in 15 ml of acetone. After complete dissolution, 85 ml of absolute ethanol are added.

The polystyrene tanks are filled with this solution. After a few minutes the liquid is eliminated by suction and the tanks are dried.

Incubation is effected as in (b) but only lasts 30 minutes.

EXAMPLE 3

Enzyme-apoprotein coupling

The lipoproteins used come from a preparative ultracentrifugation for separating the fractions according to their density.

Three different couplings have been carried out. (a) An alkaline phosphatase suspension (0.3 ml) is centrifuged in a laboratory centrifugal machine for 2 minutes. The surnatant is eliminated and the precipitate of about 1.5 ml of solid matter is dissolved in 0.2 ml of the lipoprotein solution containing about 2.3 mg of protein per milliliter.

The solution is dialyzed at 4° C. for 16 hours against a saline phosphate buffer at pH 7.4 while renewing the buffer.

10 µl of a 4.2% solution of glutaraldehyde is added in the same buffer. After 2 hours reaction at ambient temperature (20°-25° C.), the mixture is again dialyzed under the same conditions as above.

The complex collected is diluted to 4 ml by the saline phosphate buffer solution to which 1% of serum albumin is added and which contains a bactericidal agent. This solution is the one used subsequently for the measurement. In this form, the complex may be preserved at 4° C. for more than a year. The glutaraldehyde, in addition to its role of coupling agent, stabilizes the protein.
(b) a variation of the method described previously consists in effecting the coupling of two steps. In the first, the glutaraldehyde reacts in excess with one of the constituents of the complex. The excess glutaraldehyde is eliminated and the second constituent is caused to react.

(c) According to another method, when an enzyme such as peroxydase is used, it is possible to oxidize the glucid part of the enzyme with periodate to form an aldehyde function. This function allows the formation of a Schiff base with a free amine function of the protein part of the lipoprotein.

EXAMPLE 4

Method of measurement

To determine the proportion of a serum apoprotein in a sample, a vessel is used on the walls of which is fixed the antibody corresponding to this apoprotein. The vessel may be prepared extemporaneously or beforehand, as indicated previously, and preserved dry at 4° C.

The measuring medium used is the saline phosphate buffer at pH 7.4, containing 1% of bovine albumin so as to avoid parasite adsorptions and a bactericidal agent such as merthiolate or sodium nitride at the rate of 0.02%.

0.3 ml of the measuring medium are introduced into the vessel 0.5 ml either of a dilution in the same medium of the serum sample to be analyzed, or of the medium alone when a "blank" is made, or of a dilution in the same medium of standards for calibrating the determination is added. Finally 0.2 ml of a dilution to 1/250th in this medium of the lipoprotein-enzyme complex is added.

After a night of incubation, the vessels are emptied and washed three times with the buffer.

The residual enzymatic activity is measured by addition of reagents and substrates corresponding to the enzymes used.

For example, one of the following measurements may be carried out.

(a) For alkaline-phosphatase, there is added to the vessel 1 mg of p.nitrophenylphosphate in 1 ml of 0.05 M sodium carbonate buffer pH 9.8, and 1 mM $MgCl_2$.

After incubation at ambient temperature for 30 to 120 minutes, the reaction is stopped by addition of 0.1 ml of 1 M Na OH.

The absorbance is meausred with the spectrophotometer, at 480 nm, against a "blank", directly through the vessel if it provided for this use, or by transfer into appropriate tanks.

(b) The activity of the peroxydase may be measured by addition into the vessel of a solution containing 0.94 mg of phenol, 0.4 mg of amino-4-phenazone, 0.075 ml of methanol, 0.02 ml of Triton X 100 in 1 ml of 0.4 M potassium phosphate buffer, pH 7.7.

After 30 minutes incubation at ambient temperature, absorbance measurement is effected by reading at 500 nm against a blank under the same conditions as in (a).

For standardizing the determination of each apoprotein, purified apoproteins may be used directly in a given amount (by proportioning of the proteins or by gravimetry). This way of proceeding consitutes direct or primary standardizing.

As many primary standards are used as the number of distinct apoprotein measurements ($C_1$, $C_2$, $C_3$, E, $A_1$, $A_2$) it is desired to effect. Apoprotein B is difficult to obtain pure; by way of primary standard, there is used the lipoprotein isolated by ultracentrifugation in the density range of 1.043–1.055 and quantified by protein proportion.

Considering the difficulties which may arise in preparing large quantities of these primary standards, it is advantageous to use secondary standards determined by the previously described measuring method and by comparison with primary standards. These secondary standards may be constituted from human serum conserved liquid at 4° C. and containing a bactericide, or frozen or else lyophilized. This serum is calibrated for each of the apoproteins which it contains. Serum fractions per VLDL, LDL and HDL type may also be used.

EXAMPLE 5

Determination of apoprotein $C_3$ according to the method described in Example 4

The vessel used is a tube of a capacity of 2 ml made from crystal polystyrene and coated with a cellulose nitrate film in the way described in Example 2. The tubes are incubated for 30 minutes at 37° C. with an anti-apoprotein $C_3$ rabbit antiserum solution. The incubation solution (1 ml) is a sodium carbonate buffer pH 9.8, containing 2 $\mu$g in protein of the immunoglobine fraction of the antiserum.

After incubation, the tubes are washed three times with the washing buffer constituted by the saline phosphate buffer at pH 7.4, containing 0.065% of Tween 20. For each washing, the tubes are filled with the washing solution.

VLDLs isolated by ultracentrifugation at density 1.006 are coupled with alkaline phosphatase by means of glutaraldehyde in a single step.

The measuring medium is formed by the saline phosphate buffer pH 7.4 containing 1% bovine serum albumin and 0.02% of sodium nitride.

Into each tube are introduced 0.3 ml of the measuring medium, 0.5 ml of a solution "to be measured" of apoprotein $C_3$ in the same medium, and 0.2 ml of a 1/250 dilution still in the same medium of the mother solution of the VLDL-enzyme combination.

The "measured" amounts of apoproteins $C_3$ are respectively 10, 25, 50, 100 and 200 nanogrammes.

After a night's incubation at ambient temperature, the tubes are emptied and washed three times with the washing buffer.

The measurement of the enzymatic activity is made as indicated in Example 4 (a) over a time of 30 minutes.

The results of the measurements are illustrated in FIG. 1, on which the ordinate indicates the percentage of absorbance at the wave length of 480 nm with respect to a standard "blank", with the log concentration of Apoprotein being plotted on the abscissa, the said percent absorbance thus being a measurement of the amount (concentration) of Apoprotein introduced. The abscissa is on a logarithmic scale.

There can be seen, in the range of concentration considered, a good linearity of the percentage in question as a function of the logarithm of the apoprotein concentration.

The invention provides means for the determination of serum apoproteins, said determination being effected in a very specific, very sensitive way (up to 0.001 $\mu$g/ml of apoprotein expressed as nitrogen content) and with good accuracy (the measurement error is normally less than 5%).

We claim:

1. Process for the determination of serum apoproteins consisting in reacting, on the one hand, a given amount of a specific antibody of the apoprotein whose amount is to be determined, said antibody being fixed on an inert solid support, and, on the other hand, the serum sample to be analyzed and a given amount of an enzyme-lipoprotein coupling compound, corresponding to the apoprotein whose amount is to be determined, after completion of the antibody-lipoprotein reaction separating the support from the non-fixed reagents, and then measuring the enzymatic activity of the complex retained on the support, and wherein said coupling compound is formed by fixation of an enzyme on a fraction of serum lipoprotein containing several distinct apoproteins.

2. The process of claim 1 wherein the apoproteins $C_1$, $C_2$, $C_3$ and E are determined using VLDL-conjugate as the enzyme-lipoprotein coupling compound.

3. Process according to claim 1, wherein said lipoprotein fraction is either the VLDL fraction, or the LDL fraction, or the HDL fraction, such as defined in ultracentrifugation separation methods.

4. Process according to claim 1, wherein said enzyme-lipoprotein coupling compound results from coupling by means of glutaraldehyde or by formation of a Schiff base.

5. Process according to claim 1, wherein aid enzyme of the enzyme-lipoprotein compound is alkaline-phosphatase, peroxydase or galactose oxydase.

6. Process according to claim 1, wherein said antibody is fixed to the solid support in a covalent way.

7. Process according to claim 1, wherein said antibody is fixed to the support by adsorption.

8. Process according to claim 7, wherein said solid support is coated with a film of an adsorbing material.

9. Process according to claim 8, wherein said adsorption material is a cellulose or a cellulose derivative.

10. Process according to claim 1, wherein said support for the antibody is the vessel in which the analysis is effected.

11. Process according to claim 10, wherein after said antibody-lipoprotein reaction, the vessel is emptied and washed, and the reagents for measuring the enzymatic activity are introduced therein, the measurement being effected in the vessel itself.

12. A kit assembly for determination of serum apoproteins consisting essentially of at least one vessel containing at least one immobilized specific antibody of a serum apoprotein and the corresponding lipoprotein(s)-enzyme.

13. The assembly of claim 12 wherein said vessel is an hemolysis tube, a spectrophotometric tank, or a microfiltration plate.

14. The assembly of claim 13 wherein said antibody is fixed on the wall of the vessel itself.

15. The assembly of claim 12 further including at least one standard lipoprotein.

16. The assembly of claim 12 further including reagents required for measurement of enzymatic activity.

17. The assembly of claim 12 further including measuring and washing media solutions.

* * * * *